United States Patent [19]
Bossu
[11] Patent Number: 4,473,507
[45] Date of Patent: Sep. 25, 1984

[54] CONTROLLED RELEASE LAUNDRY BLEACH PRODUCT

[75] Inventor: Frank P. Bossu, West Chester, Ohio
[73] Assignee: The Procter & Gamble Company, Cincinnati, Ohio

[21] Appl. No.: 508,760
[22] Filed: Jun. 28, 1983

Related U.S. Application Data

[62] Division of Ser. No. 313,423, Oct. 21, 1981, Pat. No. 4,391,725.

[51] Int. Cl.[3] .......... C07C 179/10
[52] U.S. Cl. .......... 260/502 R
[58] Field of Search .......... 260/502 R, 502; 252/186

[56] References Cited

U.S. PATENT DOCUMENTS

| | | | |
|---|---|---|---|
| 2,362,401 | 11/1944 | Reichert et al. | 252/99 |
| 3,414,593 | 12/1968 | Robson | 260/502 R |
| 4,013,581 | 3/1977 | Huber | 252/186 |
| 4,017,411 | 4/1977 | Diehl et al. | 260/502 R |
| 4,100,095 | 7/1978 | Hutchins | 260/502 R |
| 4,126,573 | 11/1978 | Johnston | 260/502 R |
| 4,147,720 | 4/1979 | Berkowitz | 260/502 R |
| 4,179,390 | 12/1979 | Spadini | 252/95 |
| 4,233,235 | 11/1980 | Camden et al. | 260/502 R |
| 4,391,723 | 7/1983 | Bacon et al. | 252/90 |

FOREIGN PATENT DOCUMENTS

| | | | |
|---|---|---|---|
| 635620 | 1/1962 | Canada | 260/502 R |
| 18678 | 11/1980 | European Pat. Off. | 260/502 R |
| 7109629 | 1/1972 | Netherlands . | |
| 561180 | 5/1944 | United Kingdom | 260/502 R |
| 931119 | 7/1963 | United Kingdom | 260/502 R |
| 905877 | 9/1982 | United Kingdom | 260/502 R |

OTHER PUBLICATIONS

"Fine Chemicals," (Brochure) Humphrey Chemical Company, Aug. 1977, Oct. 1978.
Deutsche Coldund, "Chem. Abstract", vol. 59(1963), p. 8599.
Adam, "Chem. Abstracts", vol. 77(1972), p. 12587h.
Organic Peroxides, vol. I, pp. 335–336, Daniel Swern, 1970.
"Alkylbutanediperoxoic Acid (Alkyl-BUDIPA)", Monsanto.
Chemistry and Industry, 1961, pp. 469–470, London, Balenovic et al.

*Primary Examiner*—Werren B. Lone
*Attorney, Agent, or Firm*—Richard C. Witte; Ronald L. Hemingway

[57] ABSTRACT

A granular hydrophobic peroxyacid laundry product comprising a bleach with a surfactant bleach release agent, and an acid having a pKa of from about 2 to about 7, contained inside a pouch, bag or substrate, provides a controlled bleach release laundry product for better bleaching in a laundry wash liquor. The bleach can be an alkylmonoperoxy succinic acid.

3 Claims, 2 Drawing Figures

CONTROLLED RELEASE LAUNDRY BLEACH PRODUCT

CROSS-REFERENCE TO RELATED APPLICATION

This is a division of U.S. Ser. No. 313,423, filed Oct. 21, 1981, in the name of Frank P. Bossu now U.S. Pat. No. 4,391,725.

TECHNICAL FIELD

This invention relates broadly to bleaching compositions. This invention relates particularly to bleaching compositions which derive their bleaching activity from a compound having an active oxygen content. More particularly, this invention specifically relates to hydrophobic peroxyacid bleaching compositions contained in a pouch, bag or substrate for laundry bleaching. Still, more particularly, this invention relates to a controlled release laundry bleach product.

BACKGROUND ART

When a bagged or pouched peroxyacid bleach is dissolved or released into a laundry wash solution bleaching begins. Controlled release of the bagged or pouched peroxyacid bleach is important in various laundering systems.

POUCHED HYDROPHOBIC PEROXYACID BLEACHES

A preferred hydrophobic peroxyacid bleach is peroxydodecanoic acid (PDA). Pouched PDA releases very poorly from a pouch made of hydrophobic fibers into laundry liquor. The peroxyacid compounds of the present invention, in general, are the organic peroxyacids, water-soluble salts thereof which yield a species containing a —O—O⁻ moiety in aqueous solution, and adducts of the organic peroxyacids and urea.

Peroxyacids in general have the following formulae:

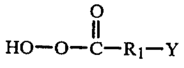 and 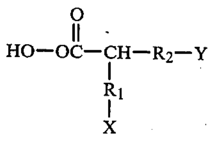

wherein $R_1$ and $R_2$ are alkylene groups containing from 1 to about 20 carbon atoms or phenylene groups, and X and Y are hydrogen, halogen, alkyl, aryl or any group which provides an anionic moiety in aqueous solution. Such X and Y groups can include, for example,

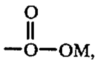, 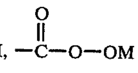 or 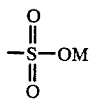

wherein M is H or a water-soluble, salt-forming cation. It is preferred that the acids used in the present invention be dried to a moisture level lower than 1.0%, and preferably lower than 0.5%.

Herein, peroxyacids are classified as either (1) hydrophobic, (2) hydrophilic, or (3) hydrotropic. In one respect, these classifications are based on their different levels of effectiveness on real world soils. Real world soils contain hydrophilic and/or hydrophobic components. A hydrophilic bleach is most effective on a hydrophilic bleachable soil, such a tea (tannic acid based), fruit juices, and the like. On the other hand, hydrophobic bleaches are most effective on hydrophobic bleachable soils, such as body soils (fatty acid/triglyceride based). Hydrotropic bleaches find utility on both types of soils, but are less effective on hydrophilic soils than hydrophilic bleaches and less effective on hydrophobic soils than hydrophobic bleaches. In another respect, a pouched hydrophobic bleach releases slowly and poorly from the pouch (as defined herein) while a pouched hydrophilic bleach releases rapidly.

A "hydrophilic bleach" is chemically defined herein as a peroxyacid whose parent carboxylic acid (or the salts thereof): (1) has no measurable critical micelle concentration (CMC) below 0.5 moles per liter (M/1) and (2) has a chromatographic retention time of less than 5.0 minutes under the following high pressure liquid chromatographic (HPLC) conditions:

> Elution with 50:50 methanol/water solvent at the rate of 1.5 ml/min. through a DuPont Zorbax ODS® column using a Waters R-401 Refractive Index Detector®.

A "hydrotropic bleach" is chemically defined as a peroxyacid whose parent carboxylic acid (or salts thereof) has no measurable CMC below 0.5M and has a chromatographic retention time of greater than 5.0 minutes under the HPLC conditions described above.

The "hydrophobic bleach" is defined as a peroxyacid whose parent carboxylic acid (or salts thereof) has a CMC of less than 0.5M. In accordance with the present invention, the CMC is measured in aqueous solution at 20°-50° C.

TABLE A

Typical Critical Micelle Concentrations For The Sodium Salts of Carboxylic Acids[1]

| | Critical Micelle Concentration[2] (Molar) |
|---|---|
| Sodium octanoate | $3.5 \times 10^{-1}$ |
| Sodium decanoate | $9.6 \times 10^{-2}$ |
| Sodium dodecanoate | $2.3 \times 10^{-2}$ |
| Sodium tetradecanoate | $6.9 \times 10^{-3}$ |
| Sodium hexadecanoate[3] | $2.1 \times 10^{-3}$ |

[1]Source: Critical Micelle Concentrations of Aqueous Surfactant Systems, NSRDS-NBS 36, 1971.
[2]25° C., aqueous solution.
[3]50° C., aqueous solution.

PUBLISHED REFERENCES

The following references will serve as background art for the present invention:

European Patent Application No. 18,678, published Nov. 12, 1980, Tan Tai Ho, discloses a bleach product comprising a percompound contained within a bag of fibrous material. The bag is coated with a protective water-permeable coating which is removable in 30°-75° C. water. Example V of the Ho EPO Patent Application discloses a coated bagged powder "diperisophthalic acid including a stabilizer (sic)." Ho reports in Example V that "the detrimental effect of diperisophthalic acid upon enzymes is delayed, and therefore improvement in enzymatic efficiency is obtained." Diperisophthalic acid is a hydrophilic peroxyacid in the context of the present invention because it releases into wash water ready from a bag without the "stabilizer."

Other useful background art is listed below.

| | Inventor | Issue Date |
|---|---|---|
| Canadian Pat. No. | | |
| 635,620 | McCune | 1/30/62 |
| U.S. Pat. No. | | |
| 3,414,593 | Robson | 12/3/68 |
| 4,017,411 | Diehl et al. | 4/12/77 |
| 4,100,095 | Hutchins | 7/11/78 |
| 4,126,573 | Johnston | 11/21/78 |

Examples of the three classes of peroxyacid bleaches are as follows:

HYDROPHOBIC PEROXYACID BLEACHES

Class a—Hydrophobic peroxyacid bleaches can include:

1 Alkyl monoperoxyacids $CH_3(CH_2)_n—CO_3H$ n=6-16, preferably 8-12; e.g., peroxydodecanoic acid wherein n=10.

For example, $C_8$-$C_{16}$ monperoxyacids belong to the hydrophobic class since the CMC of each parent acid is less than 0.5M. (Table A)

2. Alpha-substituted alkyl monoperoxyacids $CH_3—(CH_2)_n—C—CO_3H$
$\qquad\qquad\qquad\quad | $
$\qquad\qquad\qquad\quad X$ n=6-16, preferably 8-16; X=—$CH_2CO_2H$, —$CH_2CO_3H$, —$SO_3Na^+$, or —$N^+R_1R_2R_3$ and R=Hydrogen or $C_1$-$C_{16}$; e.g., 2-lauryl monoperoxysuccinic acid wherein n=11; 2-lauryl diperoxysuccinic acid wherein n=11; alpha-sulfo hexadecanoic acid wherein n=13; and alpha-tetramethylammonium hexadecanoic acid wherein n=13 and the R's=$CH_3$.

3. Aromatic peroxyacids

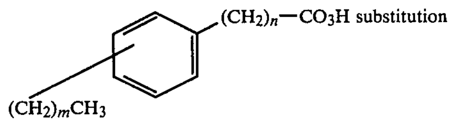

substitution in 3-5 position m=8-16, preferably 10-16; n=0-16; e.g., 4-lauryl peroxybenzoic acid.

The hydrophobic peroxyacid bleaches, those which have a long hydrocarbon chain with the percarboxylate group at one end (e.g., peroxydodecanoic acid), tend to be more effective (on an equal available oxygen basis) in the bleaching of hydrophobic stains from fabrics than those which are not constructed in this way, e.g., peroxybenzoic acid and diperoxydodecanedioic acid.

The long chain peroxyacids with the percarboxylate groups at one end have a structure similar to surface active agents (surfactants). It is believed that in a washing solution, their hydrophobic "tail" tends to be attached to the hydrophobic stains on the fabrics, thereby causing a localized increase in bleach concentration around the stain and thus resulting in increased efficiency in bleaching for a given concentration of active oxygen in the bleaching solution.

Class b—Hydrotropic peroxyacid bleaches can include:

1. Alkyl alpha, omega-diperoxyacids $HO_3C—(CH_2)_n—CO_3H$ n=8-14, preferably 9-12; e.g., diperoxydodecanedioic acid wherein n=10.

2. Alkyl monoperoxydioic acids $HO_2C—(CH_2)_n—CO_3H$ n=8-14, preferably 9-12; e.g., monoperoxydodecanedioic acid wherein n=10.

3. Aromatic diperoxyacids

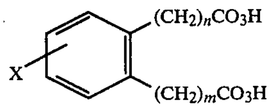

X and $-(CH_2)_mCO_3H$: substitution in 2-6 position

X=Hydrogen, Halogen or Aromatic; n+m=8-14, preferably 9-12; e.g., 1,2-(5-peroxypentanoic acid)benzene wherein m=n=5 and X=Hydrogen.

4. Aromatic monoperoxydioic acids

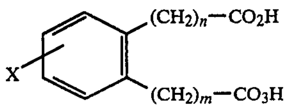

X and $-(CH_2)_nCO_3H$: substitution in 2-6 position

X=Hydrogen, Halogen or Aromatic; n+m=8-14, preferably 10-14; e.g., 1-(5-pentanoic acid)-2-(5-peroxypentanoic acid)benzene wherein m=n=5 and X=Hydrogen.

Class c—Hydrophilic peroxyacid bleaches can include:

1. Alkyl alpha, omega-diperoxyacids $HO_3C—(CH_2)_n—CO_3H$ n=2-7, preferably 2-5; e.g., diperoxyadipic acid wherein n=4.

2. Alkyl monoperoxydioic acids $HO_2C—(CH_2)_n—CO_3H$ n=2-7, preferably 2-5; e.g., monoperoxyadipic acid wherein n=4.

3. Alkyl monoperoxyacids $CH_3—(CH_2)_nCO_3H$ n=0-5, preferably 0-3; e.g., peroxybutyric acid wherein n=2.

4. Alpha-substituted monoperoxyacids $CH_3(CH_2)_n—CH—CO_3H$
$\qquad\qquad\quad | $
$\qquad\qquad\quad X$ n=0-5, preferably 0-3; X=$CH_2CO_2H$, —$CH_2CO_3H$, —$SO_3Na^+$, or —$N^+R_1R_2R_3$ and wherein any R=H or $C_1$-$C_4$; e.g., peroxypentanoic acid, 2-propyl monoperoxysuccinic acid, diperoxysuccinic acid, alpha-sulfoperoxypentanoic acid and alpha-tetramethylammonium peroxypentanoic acid, respectively, wherein n=2.

5. Aromatic monoperoxyacids

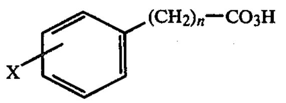

X: substitution in 2-6 position $n=0$–6, preferably 0–3; X = Hydrogen, Halogen, $-(CH_2)_mCO_2H$ or Aromatic; $m=0$–7 and $n+m=0$–7; e.g., peroxybenzoic acid wherein $n=0$ and X = Hydrogen.

6. Aromatic diperoxyacids

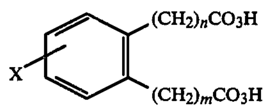

X and $-(CH_2)_mCO_3H$: substitution in 2-6 position

X = Hydrogen, Halogen or Aromatic; $n+m=0$–7, preferably 0–4; e.g., diperoxyphthalic acid wherein $n=m=0$ and X = Hydrogen.

OBJECTS

An object of the present invention is to provide a controlled release laundry bleach product which does not require a coated bag.

Another object of the present invention is to provide a pouched hydrophobic peroxyacid bleach composition that will release into a wash solution when used.

Other objects of the present invention will be apparent in the light of the following disclosure.

SUMMARY OF THE INVENTION

A dry, granular controlled release laundry bleach product in a pouch comprising:

I. a hydrophobic peroxyacid bleach; preferably peroxydodecanoic acid (PDA); and

II. an effective amount of a bleach release agent; e.g., sodium lauryl sulfate at a level of about 5% to about 60% (preferably 15% to about 55%; more preferably 30% to 50%) by weight of the hydrophobic peroxyacid to facilitate and control the release of the hydrophobic bleach from the pouch and thereby obtain better bleaching;

III. a water-soluble, peroxyacid compatible acid additive, said acid having a pKa of from about 2 to about 7, e.g., adipic acid;

wherein said pouch consists of a water-insoluble but water-permeable fibrous material, e.g., nonwoven polyester fiber with a density of 5–100 gm/m$^2$; whereby said acid additive accelerates the release of said bleach from the pouch into laundry wash liquor in the presence of said surfactant.

DETAILED DESCRIPTION OF THE INVENTION

Figure 1:
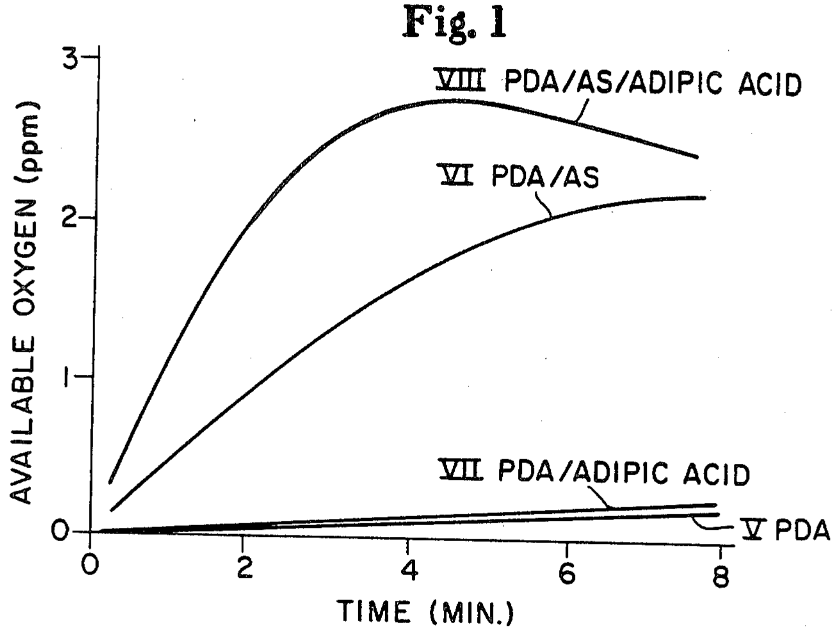
FIGS. 1 and 2 are graphs illustrating the operation of the controlled bleach release product of the present invention.

The pouched peroxyacid bleach granules component of the instant invention is normally solid, i.e., dry or solid at room temperature.

Pouched hydrophobic bleach releases poorly and slowly from the pouch into laundry wash liquor. It was surprisingly discovered that the addition of an effective amount of a surfactant, preferably sodium lauryl sulfate, from about 5% to about 60%, preferably from about 15% to about 55%, and most preferably from about 30% to about 50%, by weight of the hydrophobic bleach, dramatically increases the amount of said bleach released from the pouch.

The hydrophobic peroxyacid bleaches of this invention can include:

1. Alkyl monoperoxyacids $CH_3(CH_2)_n-CO_3H$ $n=6$–16, preferably 8–12; e.g., peroxydodecanoic acid wherein $n=10$.

For example, $C_8$–$C_{16}$ monoperoxyacids belong to the hydrophobic class since the CMC of each parent acid is less than 0.5M. (Table A)

2. Alpha-substituted alkyl monoperoxyacids

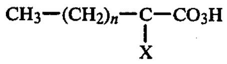

$n=6$–16, preferably 8–16; X = $-CH_2CO_2H$, $-CH_2CO_3H$, $-SO_3Na^+$, or $-N^+R_1R_2R_3$ and R = Hydrogen or $C_1$–$C_{16}$; e.g., 2-lauryl monoperoxysuccinic acid wherein $n=11$; 2-lauryl diperoxysuccinic acid wherein $n=11$; alpha-sulfo hexadecanoic acid wherein $n=13$; and alpha-tetramethylammonium hexadecanoic acid wherein $n=13$ and the R's = $CH_3$.

The alkyl radical on the alpha-substituted alkyl monoperoxyacids can be straight or branched chain. Examples of suitable alkyl radicals are hexyl, octyl, 4-methyloctyl, nonyl, 3-methylhexyl, 5-butyloctyl, decyl, lauryl, tetradecyl and hexadecyl. Preferably, the alkyl radical is a straight chain. When X in the aforedescribed alpha-substituted monoperoxyacids is $-CH_2CO_2H$, the compounds are monoperoxy succinic acids.

3. Aromatic peroxyacids

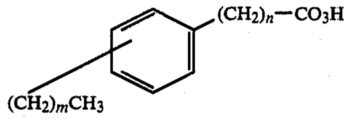

substitution in 3-5 position $m=8$–16, preferably 10–16; $n=0$–16; e.g., 4-lauryl peroxybenzoic acid.

Laundry Bleach Liquor

In typical laundry liquor, e.g., containing 64 liters of 16°–60° C. water, the pouch preferably contains a level of peroxyacid which provides about 1 to about 150 ppm available oxygen (AvO), more preferably 2–15 ppm. The laundry liquor should also have a pH of from 7 to 11, preferably 8 to 10, for effective peroxyacid bleaching.

Surfactants

It is important that peroxyacid compatible surfactants are used in the pouched bleach product of this invention. In accordance with the present invention; surfactants are incorporated into the pouched bleached compositions at levels of from about 5% to about 60%, preferably from about 15% to about 55%, and more preferably from about 30% to about 50% of the composition. Examples of suitable surfactants are given below.

Water-soluble salts of the fatty acids "soaps", are useful as the surfactant herein. This class of surfactants includes ordinary alkali metal soaps such as the sodium, potassium, ammonium and alkanolammonium salts of fatty acids containing from about 8 to about 14 carbon atoms and preferably from about 12 to about 14 carbon atoms. Soaps can be made by direct saponification of fats and oils or by the neutralization of free fatty acids. Useful are the sodium and potassium salts of the mixtures of fatty acids derived from coconut oil, i.e., sodium or potassium coconut soaps.

Another class of anionic surfactants includes water-soluble salts, particularly the alkali metal, ammonium and alkanolammonium salts, the organic sulfuric reaction products having in their molecular structure an alkyl group containing from about 8 to about 22 carbon atoms and a sulfonic acid or sulfuric acid ester group. (Included in the term "alkyl" is the alkyl portion of acyl groups.) Examples of this group of synthetic surfactants which can be used in the present bleaching compositions are the sodium and potassium alkyl sulfates, especially those obtained by sulfating the higher alcohols ($C_8$–$C_{18}$ carbon atoms) produced by reducing the glycerides of tallow or coconut oil; and sodium and potassium alkyl benzene sulfonates, in which the alkyl group contains from about 9 to about 15 carbon atoms in straight chain or branched chain configuration, e.g., those of the type described in U.S. Pat. Nos. 2,220,099, Guenther et al., issued Nov. 5, 1940; and 2,477,383, Lewis, issued July 26, 1949, incorporated herein by reference.

Other anionic surfactant compounds useful herein include the sodium alkyl glyceryl ether sulfonates, especially those ethers of higher alcohols derived from tallow and coconut oil; sodium coconut oil fatty acid monoglyceride sulfonates and sulfates; and sodium or potassium salts of alkyl phenol ethylene oxide ether sulfates containing about 1 to about 10 units of ethylene oxide per molecule and wherein the alkyl groups contain about 8 to about 12 carbon atoms.

Other useful anionic surfactants herein include the water-soluble salts of esters of $\beta$-sulfonated fatty acids containing from about 6 to about 20 carbon atoms in the ester group; water-soluble salts of 2-acyloxyalkane-1-sulfonic acids containing from about 2 to about 9 carbon atoms in the acyl group and from about 9 to about 23 carbon atoms in the alkane moiety; alkyl ether sulfates containing from about 10 to about 20 carbon atoms in the alkyl group and from about 1 to about 30 moles of ethylene oxide; water-soluble salts of olefin sulfonates containing from about 12 to about 24 carbon atoms; and $\beta$-alkyloxy alkane sulfonates containing from about 1 to about 3 carbon atoms in the alkyl group and from about 8 to about 20 carbon atoms in the alkane moiety.

Preferred water-soluble anionic organic surfactants herein include linear alkyl benzene sulfonates containing from about 11 to about 14 carbon atoms in the alkyl group; the coconut range alkyl sulfates; the coconut range alkyl glyceryl sulfonates; and alkyl ether sulfates wherein the alkyl moiety contains from about 14 to about 18 carbon atoms and wherein the average degree of ethoxylation varies between 1 and 6.

Specific preferred anionic surfactants for use herein include: sodium linear $C_{10}$–$C_{12}$ alkyl benzene sulfonate; triethanolamine $C_{10}$–$C_{12}$ alkyl benzene sulfonate; sodium coconut alkyl sulfate; sodium coconut alkyl glyceryl ether sulfonate; and the sodium salt of a sulfated condensation product of tallow alcohol with from about 3 to about 10 moles of ethylene oxide.

It is to be recognized that any of the foregoing anionic surfactants can be used separately herein or as mixtures.

Nonionic surfactants include the water-soluble ethoxylates of $C_{10}$–$C_{20}$ aliphatic alcohols and $C_6$–$C_{12}$ alkyl phenols.

Semi-polar surfactants useful herein include water-soluble amine oxides containing one alkyl moiety of from about 10 to about 28 carbon atoms and 2 moieties selected from the group consisting of alkyl groups and hydroxylakyl groups containing from 1 to about 3 carbon atoms; water-soluble phosphine oxides containing one alkyl moiety of about 10 to about 28 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 28 carbon atoms and a moiety selected from the group consisting of alkyl and hydroxyalkyl moieties of from 1 to 3 carbon atoms.

Zwitterionic surfactants include derivatives of aliphatic quaternary ammonium, phosphonium and sulfonium compounds in which the aliphatic moieties can be straight or branched chain, and wherein one of the aliphatic substituents contains from about 8 to about 18 carbon atoms and one contains an anionic water-solubilizing group.

ADVANTAGES OF POUCHED BLEACH

It was surprisingly discovered that by adding an effective surfactant to a pouched hydrophopic peroxyacid bleach composition, the otherwise partial and slow release of the bleach from the pouch into the wash liquor was increased.

A preferred dry, granular laundry bleach product in a pouch comprises:

I. a hydrophobic peroxyacid bleach (preferably PDA); and

II. a bleach release agent;

said bleach and agent being contained within a closed water-insoluble but water-permeable pouch of fibrous material; said agent consisting of a surfactant selected from the group consisting of peroxyacid compatible synthetic detergents and short chain fatty acid soaps having carbon chain lengths of from about 8 to 14, whereby said agent increases the release of said hydrophobic peroxyacid bleach from said pouch into laundry wash liquor.

The above product is more preferred when the bleach release agent is present at a level of about 5% by weight of said peroxyacid bleach, but an amount less than 5% can be an effective release agent.

The preferred peroxyacid is selected from the group consisting of: peroxydecanoic acid, peroxydodecanoic acid, and peroxytetradecanoic acid.

The preferred bleach release agent is a surfactant selected from the group consisting of: sodium lauryl sulfate, sodium laurate, and linear alkyl benzene sulfonate (LAS).

The preferred pouch of fibrous material is: polyester fibers having a density of about 5–100 $gm/m^2$ and wherein said pouch material has a pore size such that there is substantially no leakage of the granular bleach product. A more preferred fiber density is about 40–65 $gm/m^2$.

The more preferred granule comprising: PDA and sodium lauryl sulfate at a level of from about 5% to about 60% by weight of said bleach.

Another highly preferred granule comprises PDA and sodium laurate present at a level of from about 5% to about 60% by weight of said bleach.

ACID BLEACH RELEASE INCREASE AND ACCELERATING ADDITIVE

It was also surprisingly discovered that the addition of adipic acid to pouched PDA/sodium lauryl sulfate granules, further increased and accelerated the release of the pouched hydrophobic bleach. In other words, the bleach release of the pouched bleach provided by the presence of surfactant, was substantially increased by the acid additive. To obtain maximum bleaching the pouched bleach compositions should not, however, contain a level of acid additive which would adjust the pH of the wash liquor to below 7.

Suitable acid additives are water-soluble and peroxyacid compatible, and have a pKa of from about 2 to about 7, preferably from 3 to 5. Some preferred acid additives are:

| Acid | pKa |
|---|---|
| Benzoic acid | 4.2 |
| Adipic acid | 4.4/4,4 |
| Succinic acid | 4.2/5.6 |
| Citric acid | 3.1/6.0/6.4 |
| Tartaric acid | 3.0/4.3 |
| Glutaric acid | 4.3/5.4 |

The pKa's of common acids are reported on pages D-120 and 121 of *The CRC Handbook of Chem. & Physics*, 51st Edition, 1970–1971, The Chemical Rubber Co., Cleveland, Ohio, incorporated herein by reference.

As observed above, some acids have multiple pKa's. If one is in the 3 to 5 range, it can be a preferred acid additive.

A preferred dry, granular laundry bleach product in a pouch comprises:

I. a hydrophobic peroxyacid bleach,

II. a surfactant at a level of from about 5% to about 60% by weight of the peroxyacid bleach, said surfactant selected from the group consisting of peroxyacid compatible synthetic detergents and fatty acid soaps, and, III. an effective amount of a water soluble, peroxyacid compatible acid, said acid having a pKa of from about 2 to about 7, wherein said pouch consisting of water-insoluble but water-permeable fibrous material; whereby said acid accelerates the release of said bleach from the pouch into laundry wash liquor in the presence of said surfactants.

More preferred pouched peroxyacid bleach compositions contain from 20% to 60% surfactant by weight of the bleach and an effective amount of acid additive; for example, an effective amount of acid to increase the release of pouched hydrophobic bleach compositions is preferably at least about 10% by weight of the peroxyacid component of the granule, but an effective amount of acid can be less than 10% in other compositions. Highly preferred pouched bleach compositions contain surfactant at a level of 30% to 60% by weight of the peroxyacid and contain acid additive at a level of 15% to 30% by weight of the peroxyacid bleach.

The above product is highly preferred when the acid has a pKa of about 3 to about 5.

The preferred acid is selected from the group consisting of: benzoic acid, adipic acid, succinic acid, citric acid, tartaric acid, and glutaric acid.

The preferred effective amount of acid is at least about 10% by weight of the peroxyacid and where or when the product is used the laundry wash liquor maintains a pH of above 7.

The preferred peroxyacid is selected from the group consisting of: peroxydecanoic acid, peroxydodecanoic acid and peroxytetradecanoic acid.

The preferred surfactant is selected from the group consisting of: sodium lauryl sulfate, sodium laurate, and linear alkyl benzene sulfonate (LAS).

The preferred pouch of fibrous material is: polyester fibers having a density of about 5 to 100 gm/$m^2$ and wherein said pouch material has a pore size such that there is substantially no leakage of the granular bleach product. The more preferred fiber density is about 40–65 gm/$m^2$.

A preferred granule is made of: PDA and sodium lauryl sulfate at a level of from about 5% to about 60% by weight of the bleach, and wherein the acid additive is present at a level of about 10% to about 60% by weight of said bleach.

Another preferred granule is made of: PDA and sodium laurate present at a level of from about 5% to about 60% by weight of said bleach, and wherein the acid additive is present at a level of about 10% to about 60% by weight of the bleach.

Yet another preferred granule is made of: PDA, adipic acid, and sodium lauryl sulfate, wherein the latter is present at a level of about 30–60% by weight of said bleach and wherein said acid is present at a level of about 15–30% by weight of said bleach.

THE POUCH

The present invention provides a convenient bleach product contained in a closed water insoluble but waterpermeable pouch substrate, or bag of fibrous material. The bags used to form the products of the invention are the type which remain closed during the laundering process. They are formed from water insoluble fibrous-sheet material, which can be of woven, knitted, or non-woven fabric. The fabric should not disintegrate during the washing process and have a high melt or burn point to withstand the temperatures if carried over from the washer to the dryer.

The sheet material used should have a pore size such that there is substantially no leakage of the granular bleach product through the pouch material of the bag. The bleaching composition particles of this invention should be somewhat larger than the pore diameter of the porous openings in the formed bag to afford containment of the bleach admixture composition unless the pouch is coated with a coating such as those EPO Patent Application No. 18,678, Nov. 12, 1980, Tan Tai Ho, incorporated herein by reference in its entirety. Bleach compositions having an average particle diameter below about 1000 microns and preferably falling in the range from 100 to 500 microns and especially 150-300, rapidly dissolve in water and are preferred for use herein. Accordingly, pouches having an average pore diameter smaller, ca 5–50% smaller, than the particle diameter of the bleaching composition is preferred.

The fibers used for the sheet materials may be of natural or synthetic origin and may be used alone or in admixture, for example, polyester, cellulosic fibers, polyethylene, polypropylene, or nylon. It is preferred to include at least a proportion (about 20%) of thermoplastic fibers, for facilitating heat sealing of bags and resistance to chemical attack by the bleach. A suitable sheet material for forming the bags can be, for example, non-woven polyester fabric of high wet strength and a high melt or burn point weighing about 5 to 100 gm/$m^2$, preferably 40–65 gm/$m^2$.

Polyester is the preferred fiber. If more easily wettable cellulose (e.g., Rayon) or hydrophilic synthetic fibers (e.g., Nylon) are all or part of sheet material, faster release of the peroxyacid to wash liquor is expected compared to the more hydrophobic polyester sheet materials (e.g., polyester, polypropylene) at comparable densities. Thus, such hydrophilic sheet material should have a higher density for delayed pouched bleach release.

Pouches, substrates or bags can be formed from a single folded sheet formed into a tubular section or from two sheets of material bonded together at the edges. For example, the pouch can be formed from single-folded sheets sealed on three sides or from two sheets sealed on four sides. Other pouch shapes or constructions may be used. For example, compressing the bleach admixture composition between two sheets to resemble a single sheet product. Also, a tubular section of material may be filled with bleach admixture and sealed at both ends to form the closed sachet. The particular configuration (shape, size) of the pouch is not critical to the practice of this invention. For example, the pouch can be round, rectangular, square, spherical, or asymetrical. The size of the pouch is generally small. However, they can be made large for multiple uses.

OPTIONAL INGREDIENTS

Many optional ingredients are used with the product of the present invention.

A caveat is when an optional material which is inherently incompatible with the pouched peroxyacid bleach granule of this invention is included, such incompatible material should be separated from the peroxyacid component. Means for separation include: coating either the peroxyacid or the optional component, providing separate compartments in the pouch, or by coating the pouch itself with the incompatible optional material. Means for separating peroxyacid incompatible optional materials are known. See U.S. Pat. No. 4,126,573, Nov. 21, 1978, Johnston.

Detergency Builders

The instant granular compositions can also comprise those detergency builders commonly taught for use in laundry compositions. Useful builders herein include any of the conventional inorganic and organic water-soluble builder salts, as well as various water-insoluble and so-called "seeded" builders.

Inorganic detergency builders useful herein include, for example, water-soluble salts of phosphates, pyrophosphates, orthophosphates, polyphosphates, carbonates, bicarbonates, borates and silicates. Specific examples of inorganic phosphate builders include sodium and potassium tripolyphosphates, phosphates, and hexametaphosphates. Sodium tripolyphosphate is an especially preferred, water-soluble inorganic builder herein.

Nonphosphorous-containing sequestrants can also be selected for use herein as detergency builders. Specific examples of nonphosphorous, inorganic builder ingredients include water-soluble inorganic carbonate, bicarbonate, borate and silicate salts. The alkali metal, e.g., sodium and potassium, carbonates, bicarbonates, borates (Borax) and silicates are particularly useful herein.

Water-soluble, organic builders are also useful herein. For example, the alkali metal, ammonium and substituted ammonium polyacetates, carboxylates, polycarboxylates, succinates, and polyhydroxysulfonates are useful builders in the present compositions and processes. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred nonphosphorous builder materials (both organic and inorganic) herein include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Another type of detergency builder material useful in the present compositions comprises a water-soluble material capable of forming a water-insoluble reaction product with water hardness cations in combination with a crystallization seed which is capable of providing growth sites for said reaction product.

Specific examples of materials capable of forming the water-insoluble reaction product include the water-soluble salts of carbonates, bicarbonates, sesquicarbonates, silicates, aluminates and oxalates. The alkali metal, especially sodium, salts of the foregoing materials are preferred for convenience and ecomony.

Another type of builder useful herein includes various substantially water-insoluble materials which are capable of reducing the hardness content of laundering liquors, e.g., by ion-exchange processes. Examples of such builder materials include the phosphorylated cloths disclosed in U.S. Pat. No. 3,424,545, Bauman, issued Jan. 28, 1969, incorporated herein by reference.

The complex aliminosilicates, i.e., zeolite-type materials, are useful detergency builders herein in that these materials soften water, i.e., remove hardness ions. Both the naturally occurring and synthetic "zeolites," especially zeolite A and hydrated zeolite A materials, are useful for this purpose. A description of zeolite materials and a method of preparation appear in U.S. Pat. No. 2,882,243, Milton, issued Apr. 14, 1959, incorporated herein by reference.

Also useful are aminophosphonate stabilizers, which are commercially available compounds sold under the names Dequest 2000, Dequest 2041 and Dequest 2060, by The Monsanto Company, St. Louis, Mo.

These compounds have the following structures:

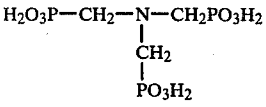

Dequest 2000

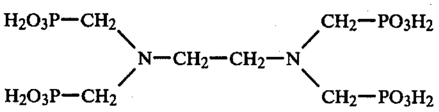

Dequest 2041

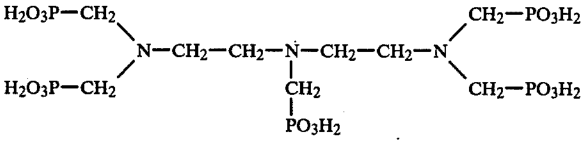

Dequest 2060

In preferred compositions of the present invention the aminophosphonate compounds can be used in their acid form, represented by the above formulas, or one or more of the acidic hydrogens can be replaced by an alkali metal ion, e.g., sodium or potassium.

Additional stabilizers can also be used, primarily to protect the peroxyacids against decomposition which is catalyzed by heavy metals such as iron and copper. Such additional stabilizing agents are preferably present at levels of from about 0.005% to about 1.0% of the composition. These additional stabilizers can be any of the well-known chelating agents, but certain ones are preferred. U.S. Pat. No. 3,442,937, Sennewald et al., issued May 6, 1969, discloses a chelating system comprising quinoline or a salt thereof, an alkali metal polyphosphate, and optionally, a synergistic amount of urea. U.S. Pat. No. 2,838,459, Sprout, Jr., issued July 10, 1959, discloses a variety of polyphosphates as stabilizing agents for peroxide baths. These materials are useful herein. U.S. Pat. No. 3,192,255, Cann, issued June 29, 1965, discloses the use of quinaldic acid to stabilize percarboxylic acids. This material, as well as picolinic acid and dipicolinic acid, would also be useful in the compositions of the present invention. A preferred auxilliary chelating system for the present invention is a mixture of 8-hydroxyquinoline or dipicolinic acid and an acid polyphosphate, preferably acid sodium pyrophosphate. The latter may be a mixture of phosphoric acid and sodium pyrophosphate wherein the ratio of the former to the latter is from about 0.2:1 to about 2:1 and the ratio of the mixture of 8-hydroxyquinoline or dipicolinic acid is from about 1:1 to about 5:1. The foregoing patents relating to stabilizers are incorporated herein by reference.

Coatings

The dry granular compositions can be coated with coating materials in order to protect them against moisture and other environmental factors which may tend to cause deterioration of the compositions when stored for long periods of time. Such coating materials may be in general, acids, esters, ethers, surfactants and hydrocarbons and include such a wide variety of materials as fatty acids, derivatives of fatty alcohols such as esters and ethers, poly functional carboxylic acids and amides, alkyl benzene sulfonates, alkyl sulfates and hydrocarbon oils and waxes. These materials aid in preventing moisture from reaching the peroxyacid compound. Secondly, the coating may be used to segregate the peroxyacid compound from other agents which may be present in the composition and which could adversely affect the peroxyacid's stability. The amount of the coating material used is generally from about 2.5% to about 20% based on the weight of the peroxyacid compound. (See U.S. Pat. No. 4,126,573, Johnston, issued Nov. 21, 1978)

Exotherm Control Agents

When subjected to excessive heat, organic peroxyacids can undergo a self-accelerating decomposition which can generate sufficient heat to ignite the peroxyacid. For this reason, it is desirable to include an exotherm control agent in peroxyacid bleaching compositions. Suitable materials include urea, hydrates of potassium aluminum sulfate and aluminum sulfate. A preferred exotherm agent is boric acid (See U.S. Pat. No. 4,100,095, Hutchins, issued July 11, 1978). The exotherm agent is preferably used in the composition at a level of from about 50% to about 400% of the amount of peroxyacid.

Miscellaneous

Various other optional ingredients such as dyes, optical brighteners, perfumes, soil suspending agents and the like may also be used in the compositions herein at the levels conventionally present in detergent and bleaching compositions.

THE EXAMPLES

The following examples illustrate the present invention but are not intended to be limiting thereof.

EXAMPLE I

1. Preparation of hydrophobic bleach adduct

The peroxydodecanoic acid (PDA)-urea adduct was prepared by mixing about a 70% aqueous mixture of peroxydodecanoic acid (PDA) with finely ground urea for about 30 minutes at about 25° C. to about 35° C., followed by removal of the water by air-drying at about 50° C. for 30 minutes and the ambient storage for 16 hours. The weight ratio of urea to peroxyacid is about 3:1. The adduct contained about 1.5% available oxygen (AvO).

2. Preparation of the bleach product

Bleach Compositions I–III were made by dry-mixing the bleach adduct with the additives as described in Table I. All the compositions include the bleach solution stabilizer, ethylenediamine (tetramethylene phosphonic acid). Compositions I and III were placed in a polyester pouch made by taking about a 76 mm×230 mm piece of polyester nonwoven substrate having a density of about 60 $g/m^2$, folding it in half and heat sealing two sides, placing bleach and additives inside and then sealing the third side to form a pouch of about 76 mm×115 mm. The nonwoven substrate used was Sontara® sold by DuPont. Composition II was added to the wash without being contained in a pouch.

3. Preparation of the bleach solution and bleach release measurements

The bleach solution was prepared using standard top-loading washing machines filled with 64.4 liters of 37.8° C. water of about 7 grain per gallon hardness. A 2.2 kg bundle of clothes was added to the tub to simulate realistic agitation effects in a normal wash. A phosphate-containing detergent (Tide®) was used at recommended levels and a single pouch was added to each wash. The products are designed to provide a maximum of about 6 ppm AvO in the wash solution when all of the bleach is released from the pouch. When required, wash aliquots were obtained at the specified times into the wash cycle to within 0.2 minutes. Bleach performance was measured by the whitening of standardized grape stained cotton swatches. The standard stain swatches were evaluated using a Hunter Color and Color Difference Meter Model D25-2 (Hunter Associates Laboratory, Inc., Fairfax, Va., USA) and reported in Hunter Whiteness Units read directly from the instrument. The higher the value the greater the degree of bleaching.

TABLE I

| BLEACH COMPOSITIONS (Grams)* | | | |
|---|---|---|---|
| Ingredients | I | II | III |
| PDA adduct | 25.9 | 25.9 | 25.9 |
| Sodium lauryl sulfate | — | — | 3.0 |
| Adipic acid | 3.0 | 3.0 | 3.0 |
| Ethylenediamine(tetramethylene phosphonic acid | 0.2 | 0.2 | 0.2 |
| Pouch | Yes | No | Yes |

*The final composition was prepared by dry-mixing the ingredients. Each composition contained enough PDA to potentially provide 6 ppm AvO in a 64.4 liter wash solution.

TABLE I-A

| BLEACH PERFORMANCE (Hunter Whiteness)* | | | |
|---|---|---|---|
| Swatch | I | II | III |
| Grape on cotton | 26.6 | 43.3 | 53.1 |

*Average of six swatches.

Table I-A summarizes the bleach performance. Composition I provided poorer performance than the direct addition of the same material (Composition II). The addition of sodium lauryl sulfate to Composition I results in Composition III and the bleach performance results in Table I-A show significant advantages for Composition III over Composition I, as well as the direct addition (Composition II).

EXAMPLE II

1. Preparation of hydrophobic bleach adduct

The method of preparation of the urea adduct of peroxydodecanoic acid is the same as described in Example I, paragraph 1. Upon analysis the peroxyacid adduct was determined to contain 1.7% AvO.

2. Preparation of bleach compositions, bleach solutions and measurement of peroxyacid release The bleach Compositions IV–VIII were prepared by dry-mixing the ingredients listed in Table II and placing the dry mix in pouches as described in Example I, paragraph 2. The dry mix had enough bleach to potentially deliver 6 ppm AvO to a 64.4 liter wash solution. Compositions V–VIII contain a peroxyacid stabilizer, ethylenediamine(tetramethylene phosphonic acid). The stabilizer is not necessary for controlled release of the bleach, but is highly preferred for a stabilized bleach solution.

TABLE II

| COMPOSITIONS PER POUCH (Grams) | | | | | |
|---|---|---|---|---|---|
| Ingredients | IV | V | VI | VII | VIII |
| PDA adduct | 23.5 | 23.5 | 23.5 | 23.5 | 23.5 |
| Ethylenediamine (tetramethylene phosphonic acid) | — | 0.25 | 0.25 | 0.25 | 0.25 |
| Sodium lauryl sulfate | — | — | 3.0 | — | 3.0 |
| Adipic acid | — | — | — | 3.0 | 3.0 |

TABLE II-A

| AvO IN WASH SOLUTION (ppm)* | | | | | |
|---|---|---|---|---|---|
| Time (Minutes) | IV | V | VI | VII | VIII |
| 1.5 | 0.2 | 0.1 | 0.8 | 0.1 | 1.6 |
| 4.0 | 0.3 | 0.1 | 1.4 | 0.2 | 2.8 |
| 6.5 | 0.4 | 0.2 | 2.2 | 0.2 | 2.3 |
| 10.3 | 0.4 | 0.2 | 2.1 | 0.3 | 1.8 |

*Average of three replicates.

The wash solution bleach concentrations for Compositions IV–VIII are reported in terms of ppm AvO in Table II-A. Compositions IV with the bleach alone, releases only very low levels (0.2 to 0.4) to the wash leaving some active in the pouch after the wash without release to the wash for useful bleaching. A comparison of the AvO results for Compositions IV, V, and VII indicates that low levels of the stabilizer, or the stabilizer with adipic acid at 57% of the bleach level, do not increase the amount of peroxydodecanoic acid released from the pouch in the presence of the adduct alone. Composition VII shows that the addition of sodium lauryl sulfate at about 57% of the peroxyacid to the peroxyacid adduct and stabilizer in the pouch increases the amount of peroxyacid in the wash by a factor of about 7 to 11 at different times in the wash. The addition of adipic acid and sodium lauryl sulfate at a level of 57% of the peroxyacid (Composition VIII) further increases the amount of bleach in the wash by a factor of 2 in the first four minutes of the wash compared to Composition VI without adipic acid and only sodium lauryl sulfate as an additive. A comparison of AvO results for Compositions V–VIII shows that the boosting effect of adipic acid is only observed when combined in the admixture with a surfactant and the hydrophobic bleach. Compositions VI and VIII totally release by the end of the wash cycle.

EXAMPLE III

1. Preparation of bleach product

The preparation of the urea adduct of the hydrophobic peroxyacid, peroxydodecanoic acid, is described in Example I, paragraph 1.

Bleach Compositions IX–XII were prepared to show the effect of different surfactant additives on the release of the peroxyacid and they are described in Table III. These compositions were dry-mixed and placed in the pouches described in Example I, paragraph 2.

2. Preparation of bleach solution and peroxyacid release measurements

The bleach solutions were prepared in the same manner as in Example I, paragraph 3, except that the wash solution temperature was about 33° C. The products of Compositions IX–XII are designed to provide a maximum of about 6 ppm AvO in the wash.

TABLE III

| | COMPOSITIONS PER POUCH (Grams) | | | |
|---|---|---|---|---|
| Ingredients | IX | X | XI | XII |
| PDA adduct | 25.9 | 25.9 | 25.9 | 25.9 |
| Ethylenediamine (tetramethylene phosphonic acid) | 0.2 | 0.2 | 0.2 | 0.2 |
| $C_{11.7}$ LAS | 2.0 | — | — | — |
| Sodium lauryl sulfate | — | 2.0 | — | — |
| Tallow alkyl sulfate | — | — | 2.0 | — |
| Sodium petroleum sulfonate | — | — | — | 2.0 |

TABLE III-A

| | AvO IN WASH SOLUTION (ppm) | | | |
|---|---|---|---|---|
| Time (Minutes) | IX | X | XI | XII |
| 0.7 | 0.9 | 1.8 | 0.4 | 0.4 |
| 1.5 | 1.5 | 3.4 | 0.8 | 0.5 |
| 3.5 | 3.5 | 3.3 | 1.6 | 1.6 |
| 5.7 | 2.6 | 2.7 | 2.5 | 1.8 |
| 8.0 | 2.1 | 2.2 | 2.6 | 2.8 |

The wash solution concentrations for Compositions IX–XII are reported in Table III-A. The results show that the addition of different types of surfactants at about 38% of the peroxyacid level to peroxydodecanoic acid adduct with stabilizer in a pouch, provides varying levels of bleach throughout the wash cycle. The granular active is substantially gone from the pouch after the wash cycle for all of the surfactant additive systems (Compositions X–XII).

EXAMPLE IV

The effect of surfactant level on release of peroxydodecanoic acid from a pouch was studied with sodium lauryl sulfate in the presence of adipic acid. Compositions XIII–XVI were prepared by dry-mixing the ingredients described in Table IV. The bleach adduct used was the same as described in Example I, paragraph 1. The compositions were placed in pouches as described in Example I, paragraph 2. The preparation of the bleach solution and the bleach release measurements were obtained in the same manner described in Example I, paragraph 3.

TABLE IV

| | COMPOSITIONS PER POUCH (Grams) | | | |
|---|---|---|---|---|
| Ingredient | XIII | XIV | XV | XVI |
| PDA adduct | 25.9 | 25.9 | 25.9 | 25.9 |
| Ethylenediamine (tetramethylene phosphonic acid) | 0.2 | 0.2 | 0.2 | 0.2 |
| Adipic acid | 2.0 | 2.0 | 2.0 | 2.0 |
| Sodium lauryl sulfate | — | 0.5 | 1.0 | 3.0 |

TABLE IV-A

| | AvO IN WASH SOLUTION (ppm) | | | |
|---|---|---|---|---|
| Time (Minutes) | XIII | XIV | XV | XVI |
| 0.7 | 0.2 | 0.6 | 0.4 | 1.2 |
| 1.7 | 0.3 | 0.9 | 1.8 | 3.2 |
| 3.4 | 0.4 | 1.6 | 2.0 | 3.7 |
| 5.5 | 0.4 | 1.7 | 2.7 | 2.9 |
| 8.0 | 0.5 | 1.8 | 2.6 | 2.4 |

The wash solution concentrations of bleach for Compositions XIII–XVI are summarized in Table IV-A. The results show that increasing the level of sodium lauryl sulfate from about 9% of the peroxyacid level (Composition XIV), to about 19% of the peroxyacid level (Composition XV) and more, to about 57% of the peroxyacid level (Composition XVI) provides increasingly faster release and a greater amount of bleach in solution. All of these compositions with sodium lauryl sulfate released more bleach to the wash than Composition XIII which did not contain any surfactant.

EXAMPLE V

The effect of surfactant, without adipic acid present, when added to the bleach was measured by the release of the bleach from a pouch and the bleach performance as measured by the whitening of standardized grape and coffee stained swatches of a variety of fabric types. Compositions XVII and XVIII were prepared by dry-mixing the ingredients described in Table V. The bleach adduct used was the same as described in Example I, paragraph 1, and measured to have about 1.5% AvO. Both compositions contained enough PDA to provide a maximum 6 ppm AvO in a 64.4 liter wash solution. The compositions were sealed in pouches as described in Example I, paragraph 2. The preparation of the bleach solution and the bleach release measurements were obtained in the same manner described in Example I, paragraph 3.

TABLE V

| | COMPOSITIONS PER POUCH (Grams) | |
|---|---|---|
| Ingredients | XVII | XVIII |
| PDA adduct | 26.4 | 26.4 |
| Ethylenediamine (tetramethylene phosphonic acid) | 0.25 | 0.25 |
| Sodium lauryl sulfate | 3.0 | — |

TABLE V-A

| | AvO IN WASH SOLUTION (ppm) | |
|---|---|---|
| Time (Minutes) | XVII | XVIII |
| 1.0 | 0.5 | 0.3 |
| 2.7 | 2.0 | 0.4 |
| 5.0 | 2.8 | 0.5 |
| 8.0 | 3.3 | 0.6 |

TABLE V-B

| | BLEACH PERFORMANCE (Hunter Whiteness)* | |
|---|---|---|
| Swatch | XVII | XVIII |
| Grape on cotton | 34.8 | 32.1 |
| Grape on polyester | 84.1 | 76.6 |
| Grape on polycotton | 50.6 | 47.1 |
| Coffee on cotton | 23.2 | 21.4 |
| Coffee on polyester | 106.3 | 105.6 |
| Coffee on polycotton | 50.2 | 43.9 |

*Average of six swatches.

Tables V-A and V-B illustrate the differences in bleach release and performance for Compositions XVII and XVIII. The addition of sodium lauryl sulfate in the pouch (XVII) resulted in more bleach released to the wash during the wash cycle and improved bleach cleaning for Composition XVII compared to Composition XVIII.

EXAMPLE VI

The alpha-substituted monoperoxy acids of the formula $$CH_3-(CH_2)_n-\underset{\displaystyle X}{\underset{|}{C}}-CO_3H$$

wherein X is $-CH_2CO_2H$ (i.e., the alkylmonoperoxy succinic acids) can be prepared by general procedures described in the art for preparing monoperoxyacids from the corresponding dicarboxylic acids or their anhydrides. See *Organic Syntheses,* Vol. 20, Page 70 (1940); Bachman, *J. Org. Chem.,* Vol. 9, Pages 302–309 (1944); and Ogata et al., *Tetrahedron,* Vol. 23, Page 3327 (1967), all incorporated herein by reference. Examples of preferred alkylmonoperoxy succinic acids are octyl-, decyl-, lauryl and tetradecylmonoperoxy succinic acid.

Alkyl succinic anhydrides which serve as suitable starting materials for making the alkylmonoperoxy succinic acids herein can be prepared by reaction of an olefin with maleic anhydride to form the corresponding alkenyl succinic anhydride, which can be reduced to the alkyl succinic anhydride with hydrogen. The anhydride can, if desired, be converted to the corresponding acid by simple hydrolysis. One commercial source of alkyl succinic anhydrides useful in preparing the alkylmonoperoxy succinic acids herein is Humphrey Chemical Company, North Haven, CT.

Although the alkylmonoperoxy succinic acids have been described hereinbefore in the context of bleaching compositions in a pouch, their use as bleaches is not limited to that context. They can be used in the same manner as other known bleaches in the treatment of fabrics, bleaching of pulp, etc. As described in European Pat. Appln. No. 68547, published Jan. 5, 1983 (incorporated by reference herein) when bleaching fabrics which contain hydrophobic soils (e.g., body oils) and hydrophilic soils (e.g., fruit juice stains) it can be advantageous to use the bleaches of the present invention, which are hydrophobic, in combination with hydrophilic bleaches such as diperoxyadipic acid and/or hydrotropic bleaches such as diperoxydodecanedioic acid. Typically, the peroxyacid bleaches are used at a level which will produce about 5–15 ppm available oxygen in the bleaching solution.

Preparations of specific alkylmonoperoxy succinic acids are illustrated in the following examples.

VIa. Preparation of Tetradecylmonoperoxy Succinic Acid

To 150 mls of water in a beaker equipped with a magnetic stirrer were added 6 gms of sodium hydroxide and 0.25 gm of magnesium sulfate heptahydrate. The mixture was stirred until totally dissolved. Maintaining the solution at about room temperature (20±5° C.) with an ice bath, 9 mls of 50% hydrogen peroxide was slowly added. 14.8 gms of tetradecyl succinic anhydride, finely ground, were then added with rapid stirring. The solids were almost entirely dissolved in 15 minutes and the reaction was quenched at 19 minutes with 150 mls of a 20% $H_2SO_4$ solution. The reaction mix was cooled to about 15° C. and the precipitate, containing tetradecylmonoperoxy succinic acid was isolated by filtration.

The isolation by filtration involved use of a standard buchner funnel and filter paper under aspirator vacuum. The solid was washed 3 times with cold water. The isolated wet cake was measured by standard methods to have an available oxygen content of 1.4%. The wet cake was determined to be 61% solids based upon water removal by drying. Based on the available oxygen level, the solid was calculated to be 47% tetradecylmonoperoxy succinic acid.

The same reaction as above was repeated, except that isolation of the monoperoxyacid was by chloroform extraction. After quenching and cooling of the reaction mix, the reaction mix was extracted three times with 50 mls of chloroform. The emulsion that formed upon shaking was dissipated with a small amount of methanol. The chloroform extracts were combined and the solvent was removed by passing a nitrogen stream over the solution. The dried solid was collected and analyzed by standard methods to have an available oxygen content of 2.53%. Thus, the solid contained 52% of the tetradecylmonoperoxy succinic acid.

VIb. Preparation of Dodecylmonoperoxy Succinic Acid

Dodecylmonoperoxy succinic acid (also called laurylmonoperoxy succinic acid) may be prepared in the following manner.

75 mls of methanol is added to 60 mls of water in a 500 ml beaker equipped with magnetic stirrer. 0.5 gm of magnesium sulfate heptahydrate and 12.0 gms of a 50% sodium hydroxide solution are added and stirred until totally dissolved. 9.0 mls of a 50% hydrogen peroxide solution is slowly added to the reaction mix, while maintaining the solution temperature at 20±5° C. 13.3 gms of finely ground dodecyl succinic anhydride is then added with rapid stirring. Reaction is continued until anhydride solubilizes (about 10–15 minutes) and the reaction is then quenched with 150 mls of a 20% $H_2SO_4$ solution. The reaction mix is then extracted with three 50 ml portions of chloroform. The chloroform extracts are combined and the solvent is removed by passing a nitrogen stream over the solution. The dry solid that remains contains dodecylmonoperoxy succinic acid.

DETAILED DESCRIPTION OF THE DRAWINGS

Figure 2:
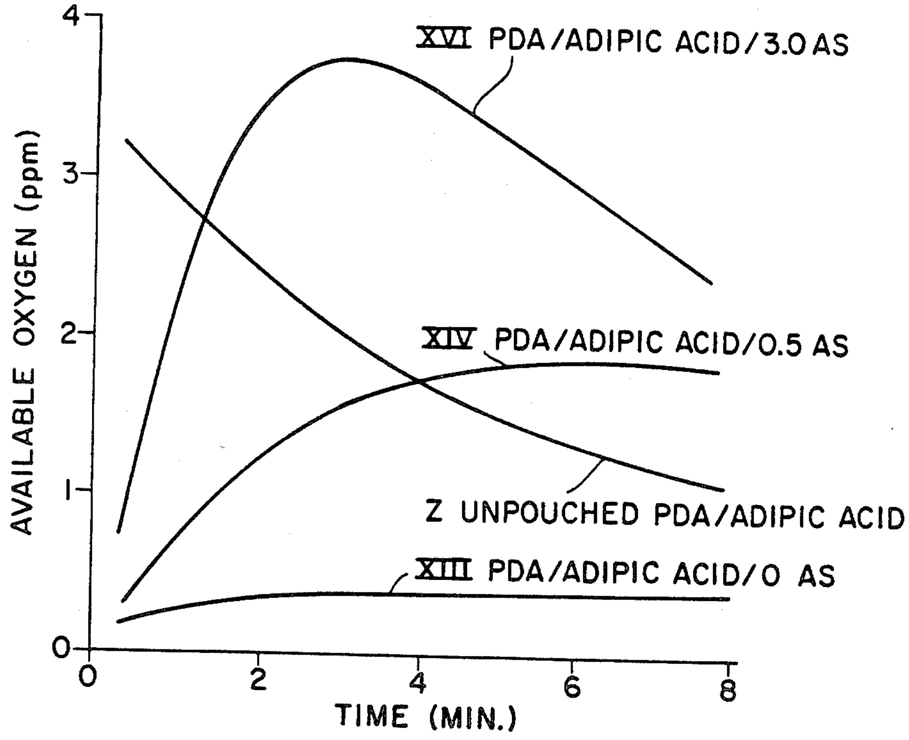

The curves in FIGS. 1 and 2 are identified by numbers corresponding to the composition numbers in the examples. "AS" is alkyl sulfate, specifically sodium lauryl sulfate.

In FIG. 1 curves V, VI, VII and VIII illustrate available oxygen (AvO) in ppm vs. time (min.) in wash solutions for various pouched PDA. Each contained PDA to deliver AvO of a potential level of 6 ppm. Curves V, VI, VII and VIII, respectively, represent AvO vs. time for PDA alone (V), PDA plus lauryl sulfate (VI), PDA plus adipic acid (VII) and PDA plus lauryl sulfate plus adipic acid (VIII). V vs. VI illustrate the dramatic increase of bleach release by adding surfactant to the pouch. VII vs. VIII illustrate faster and more bleach release with adipic acid plus surfactant added to the pouch.

Referring now to FIG. 2, the numbered curves are plotted from Table II-A. Curve Z is unpouched, i.e., direct addition of PDA to a wash solution, at a potential AvO level of 6 ppm with 2.0 gms adipic acid also added. Curve XIII is pouched PDA plus 2 gms adipic acid without surfactant. Curve XIV is PDA plus 2 gms adipic acid plus 0.5 gm (~9% by weight of PDA) lauryl sulfate. XVI is the same as XIV, except that lauryl sulfate is present at a level of 3.0 gms (~55% by weight of PDA).

Thus, it is shown in Table II-A and FIG. 2 that the higher surfactant levels increase the release of bleach—XVI vs. XIV vs. XIII. Also, the pouched bleach compositions of this invention (XIV and XVI) illustrate superior controlled bleaching over unpouched bleach "Z" and pouched bleach without surfactant (XIII).

What is claimed is:

1. A granular bleach compound of the formula

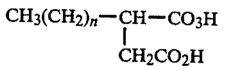

wherein n is from about 6 to about 16.

2. The compound of claim 1 wherein n is from about 8 to about 16.

3. The compound of claim 2 wherein $CH_3(CH_2)_n$ is lauryl.

* * * * *

UNITED STATES PATENT AND TRADEMARK OFFICE

CERTIFICATE OF CORRECTION

PATENT NO. : 4,473,507

DATED : September 25, 1984

INVENTOR(S) : Frank P. Bqssu

It is certified that error appears in the above-identified patent and that said Letters Patent are hereby corrected as shown below:

In the title, before "CONTROLLED" insert -- ALKYLMONOPEROXY SUCCINIC ACIDS AND THEIR USE IN --.

Col. 1, in the title, before "CONTROLLED" insert -- ALKYLMONO-PEROXY SUCCINIC ACIDS AND THEIR USE IN --.

Col. 3, line 30 and Col. 6, line 20 the formula

"$CH_3 - (CH_2)_n - \underset{X}{\underset{|}{C}} - CO_3H$ " should be

-- $CH_3 - (CH_2)_n - \underset{X}{\underset{|}{CH}} - CO_3H$ --.

Signed and Sealed this

*Ninth* Day of *July 1985*

[SEAL]

*Attest:*

DONALD J. QUIGG

*Attesting Officer* *Acting Commissioner of Patents and Trademarks*